(12) United States Patent
Babico

(10) Patent No.: US 11,833,363 B2
(45) Date of Patent: Dec. 5, 2023

(54) CURRENT-BASED RF DRIVER FOR PULSED ELECTROMAGNETIC FIELD APPLICATOR SYSTEMS

(71) Applicant: Regenesis Biomedical, Inc., Scottsdale, AZ (US)

(72) Inventor: John Y. Babico, Scottsdale, AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 0 days.

(21) Appl. No.: 17/080,815

(22) Filed: Oct. 26, 2020

(65) Prior Publication Data

US 2021/0121711 A1    Apr. 29, 2021

Related U.S. Application Data

(60) Provisional application No. 62/926,375, filed on Oct. 25, 2019.

(51) Int. Cl.
*A61N 2/02* (2006.01)
*G06K 7/10* (2006.01)

(52) U.S. Cl.
CPC ........... *A61N 2/02* (2013.01); *G06K 7/10366* (2013.01)

(58) Field of Classification Search
CPC .......... A61N 1/326; A61N 1/40; A61N 2/004; A61N 2/02
See application file for complete search history.

(56) References Cited

U.S. PATENT DOCUMENTS

| | | | |
|---|---|---|---|
| 4,926,881 A | 5/1990 | Ichinomiya et al. | |
| 5,000,178 A | 5/1991 | Griffith | |
| 5,314,401 A | 5/1994 | Tepper | |
| 6,132,362 A | 10/2000 | Tepper et al. | |
| 6,162,166 A * | 12/2000 | Neuwirth | A61N 2/02 600/14 |
| 6,174,276 B1 | 1/2001 | Blackwell | |
| 6,261,221 B1 | 7/2001 | Tepper et al. | |
| 6,334,069 B1 | 12/2001 | George et al. | |
| 6,443,883 B1 | 9/2002 | Ostrow et al. | |
| 6,463,336 B1 | 10/2002 | Mawhinney | |
| 6,967,281 B2 | 11/2005 | George et al. | |
| 6,974,961 B1 | 12/2005 | George et al. | |
| 7,907,701 B2 | 3/2011 | Anderson | |
| 8,195,287 B2 | 6/2012 | Dacey et al. | |
| 10,245,439 B1 * | 4/2019 | Schwarz | A61N 2/02 |

(Continued)

FOREIGN PATENT DOCUMENTS

WO    WO2012/048302 A2    4/2012
WO    WO2020/222020 A1    11/2020

OTHER PUBLICATIONS

Akan et al.; Extremely low-frequency electromagnetic fields affect the immune response of monocyte-derived macrophages to pathogens; Bioelectromagnetics; 31(8); pp. 603-612; Dec. 2010.

(Continued)

*Primary Examiner* — Christine H Matthews
(74) *Attorney, Agent, or Firm* — Shay Glenn LLP

(57) ABSTRACT

The apparatuses can comprise a controller including a RF driver configured to generate a pulsed current signal and one or more applicators coupled to the controller. Each applicator can include a coil circuit configured to receive the pulsed current signal and to emit a pulsed electromagnetic field signal comprising a magnetic field signal.

20 Claims, 5 Drawing Sheets

(56) References Cited

U.S. PATENT DOCUMENTS

| | | | |
|---|---|---|---|
| 10,263,466 | B2 | 4/2019 | Boys et al. |
| 10,441,807 | B2 | 10/2019 | Moffett |
| 10,773,094 | B1* | 9/2020 | Rzasa .............. G06K 19/0723 |
| 2004/0176805 | A1 | 9/2004 | Whelan et al. |
| 2004/0210254 | A1* | 10/2004 | Burnett .................. A61N 1/40 |
| | | | 607/2 |
| 2005/0010163 | A1 | 1/2005 | Aoki et al. |
| 2005/0059153 | A1 | 3/2005 | George et al. |
| 2007/0060981 | A1 | 3/2007 | Pilla et al. |
| 2008/0004904 | A1 | 1/2008 | Tran |
| 2008/0249350 | A1* | 10/2008 | Marchitto .............. A61N 2/02 |
| | | | 600/10 |
| 2009/0228071 | A1 | 9/2009 | Bourget |
| 2011/0065976 | A1 | 3/2011 | Chomenky et al. |
| 2011/0112352 | A1 | 5/2011 | Pilla et al. |
| 2011/0196365 | A1 | 8/2011 | Kim et al. |
| 2012/0116149 | A1 | 5/2012 | Pilla et al. |
| 2012/0302821 | A1 | 11/2012 | Burnett |
| 2013/0006039 | A1* | 1/2013 | Sadler ................... A61N 2/006 |
| | | | 600/14 |
| 2013/0190599 | A1 | 7/2013 | Wyeth et al. |
| 2013/0245486 | A1 | 9/2013 | Simon et al. |
| 2014/0012108 | A1 | 1/2014 | McPeak |
| 2014/0148870 | A1 | 5/2014 | Burnett |
| 2014/0213844 | A1 | 7/2014 | Pilla et al. |
| 2014/0249355 | A1 | 9/2014 | Martinez |
| 2014/0265611 | A1 | 9/2014 | Fern et al. |
| 2014/0336443 | A1 | 11/2014 | Maharaj |
| 2014/0367270 | A1 | 12/2014 | Williamson |
| 2015/0018643 | A1 | 1/2015 | Cole et al. |
| 2015/0297910 | A1 | 10/2015 | Dimino et al. |
| 2016/0015995 | A1 | 1/2016 | Leung et al. |
| 2016/0346561 | A1 | 12/2016 | Ron Edoute et al. |
| 2018/0043174 | A1 | 2/2018 | Gurfein |
| 2018/0071545 | A1* | 3/2018 | Saitoh ................... A61N 2/008 |
| 2018/0126185 | A1 | 5/2018 | Hochstenbach |
| 2018/0318598 | A1* | 11/2018 | Russo ................. G06K 19/0723 |
| 2019/0192873 | A1* | 6/2019 | Schwarz .................. A61F 7/00 |
| 2019/0217090 | A1 | 7/2019 | Ryaby et al. |
| 2019/0290925 | A1 | 9/2019 | Gellman et al. |
| 2019/0388676 | A1 | 12/2019 | Babico |
| 2020/0001101 | A1 | 1/2020 | Moffett |
| 2020/0139120 | A1 | 5/2020 | Rajguru et al. |
| 2020/0206523 | A1 | 7/2020 | Kirk et al. |
| 2020/0360710 | A1 | 11/2020 | Anderson et al. |
| 2022/0118268 | A1 | 4/2022 | Kirk et al. |
| 2022/0409917 | A1 | 12/2022 | Kirk et al. |

OTHER PUBLICATIONS

Apfelbaum et al.; Postoperative pain experience: results from a national survey suggest postoperative pain continues to be undermanaged; Anesthesia and Analgesia; 97(2); pp. 534-540; Aug. 2003.

Baranano et al.; Biliverdin reductase: a major physiologic cytoprotectant; Proceedings of the National Academy of Sciences; 99(25); pp. 16093-16098; Dec. 10, 2002.

Basbaum et al.; Cellular and molecular mechanisms of pain; Cell; 139(2); pp. 267-284; Oct. 16, 2009.

Brennan et al.; Cytokine expression in chronic inflammatory disease; British Medical Bulletin; 51(2); pp. 368-384; Apr. 1995.

Buckley et al.; The resolution of inflammation; Nature Reviews Immunology; 13(1); pp. 59-66; Jan. 2013.

Catala; Five decades with polyunsaturated Fatty acids: chemical synthesis, enzymatic formation, lipid peroxidation and its biological effects; Journal of Lipids; http://dx.doi.org/10.1155/2013/710290; 20 pages; (year of pub. sufficiently earlier than effective US filing date and any foreign priority date) 2013.

Clark et al.; Neuropathic pain and cytokines: current perspectives; Journal of Pain Research; 6; pp. 803-814; doi: 10.2147/JPR.S53660; 12 pages; Nov. 21, 2013.

Commins et al.; The extended IL-10 superfamily: IL-10, IL-19, IL-20, IL-22, IL-24, IL-26, IL-28, and IL-29; Journal of Allergy and Clinical Immunology: 121(5); pp. 1108-1111; May 2008.

Dutra et al.; Heme on innate immunity and inflammation; Frontiers in Pharmacology; 5; Article 115; doi: 10.3389/fphar.2014.00115; 20 pages; May 2014.

Gou et al.; Meta-analysis of clinical efficacy of pulsed radio frequency energy treatment; Annals of Surgery; 255(3); pp. 457-467; Mar. 2012.

Greene et al.; Regulation of inflammation in cancer by eicosanoids; Prostaglandins and Other Lipid Mediators; 96(1-4); pp. 27-36; 26 pages; (Author Manuscript); Nov. 2011.

Guo et al.; Pulsed radio frequency energy (PRFE) use in human medical applications; Electromagnetic Biology and Medicine; 30(1); pp. 21-45; Mar. 2011.

Hasegawa et al.; Modifying TNF alpha for therapeutic use: a perpective on the TNF receptor system; Mini Reviews in Medicinal Chemistry; 1(1); pp. 5-16; May 2001.

Haworth et al.; Resolving the problem of persistence in the switch from acute to chronic inflammation; Proceedings of the National Academy of Sciences; 104(52); pp. 20647-20648; Dec. 26, 2007.

He et al.; Exposure to extremely low-frequency electromagnetic fields modulates Na+ currents in rat cerebellar granule cells through increase of AA/PGE2 and EP receptor-mediated cAMP/PKA pathway; Plos One; 8(1); pp. e54376; 13 pages; Jan. 22, 2013.

Heden et al.; Effects of pulsed electromagnetic fieldis on postoperative pain: a double-blind randomized pilot study in breast augmentation patients; Aesthetic Plastic Surgery; 32(4); pp. 660-666; Jul. 2008.

Ji et al; Emerging roles of resolvins in the resolution of inflammation and pain; Trenads in Neurosciences; 34(11); pp. 599-609; 20 pages; (Author Manuscript); Nov. 2011.

Kunkel et al.; Suppression of acute and chronic inflammation by orally administered prostaglandins; Arthritis and Rheumatism: Official Journal of the American College of Eheumatology; 24(9); pp. 1151-1158; Sep. 1981.

Livak et al.; Analysis of relative gene expression data using real-time quantitative PCR and the 2-??CT method; Methods; 25(4); pp. 402-408; Dec. 2001.

Markov et al.; Interaction between electromagnetic fields and the immune system: possible mechanisms for pain control; Ayrapetyan Snm, M.S., ed.; Bioelectromagnetics Current Concepts; Dordrecht: Springer; pp. 213-225; (year of pub. sufficiently earlier than effective US filing date and any foreign priority date) 2006.

McIntyre et al.; Molecular mechanisms of early inflammation; Thromb Haemost; 78(I):302-305; Jul. 1997.

Medzhitov et al.; Transcriptional control of the inflammatory response; Nature Reviews Immunology; 9(10); pp. 692-703; Oct. 2009.

Medzhitov: Origin and physiological roles of inflammation; Nature; 454(7203); pp. 428-435; Jul. 23, 2008.

Medzhitov; Inflammation 2010: new adventures of an old flame; Cell; 140(6); pp. 771-776; Mar. 19, 2010.

Moffett et al.; Activation of endogenous opioid gene expression in human keratinocytes and fibroblasts by pulsed radiofrequency energy fields; Journal of Pain Research; 5; pp. 347-357; Sep. 19, 2012.

Moffett et al.; Pulsed radio frequency energy field treatment of cells in culture results in increased expression of genes involved in angiogenesis and tissue remodeling during wound healing; The Journal of Diabetic Foot Complications; 3(2); pp. 30-39; (year of pub. sufficiently earlier than effective US filing date and any foreign priority date) 2011.

Moffett et al.; Pulsed radio frequency energy field treatment of cells in culture results in increased expression of genes involved in inflammation phase of lower extremity diabetic wound healing; The Journal of Diabetic Foot Complications; 2(3); pp. 57-64; (year of pub. sufficiently earlier than effective US filing date and any foreign priority date) 2010.

Moreland; Inhibitors of tumor necrosis factor for rheumatoid arthritis; 66(6); pp. 367-374; Jun. 1999.

Moreland; Inhibitors of tumor necrosis factor for rheumatoid arthritis; The Journal of Rheumatology; 57; pp. 7-15; May 1, 1999.

Mosser et al.; Interleukin-10: new perspectives on an old cytokine; Immunological Reviews; 226(1); pp. 205-218; 22 pages; (Author Manuscript); Dec. 2008.

Nathan; Nonresolving inflammation; Cell; 140(6); pp. 871-882; Mar. 19, 2010.

(56) References Cited

OTHER PUBLICATIONS

Neher et al.; Molecular mechanisms of inflammation and tissue injury after major traumais complement the "bad guy" ?; Journal of Biomedical Sciences; 18(1); pp. 90; doi: 10.1186/1423/1423-0127-18-90; Dec. 2011.
Novo et al.; Redox mechanisms in hepatic chronic wound healing and fibrogenesis; Fibrogenesis and tissue repair; 1(1); doi:10.1186/1755-1536-1-5; 58 pages; Dec. 2008.
Pelletier et al.; New tricks from an old dog: mitochondria) redox signaling in cellular inflammation; InSeminars in Immunology; 24(6); pp. 384-392; 21 pages; (Author Manuscript); Dec. 2012.
Pilla et al.; EMF signals and ion/ligand binding kinetics: prediction of bioeffective waveform parameters; Bioelectrochemisrty and Bioenergetics; 48(1); pp. 27-34; Feb. 1999.
Pilla et al.; Nonthermal electromagnetic fields: from first messenger to therapeutic applications; Electromagnetic Biology and Medicine; 32(2); pp. 123-136; Jun. 2013.
Pons et al.; Pro-inflammatory and anti-inflammatory effects of the stable prostaglandin D2 analogue; European Journal of Pharmacology; 261(3); pp. 237-247; Aug. 22, 1994.
Rohde et al.; Effects of pulsed electromagnetic fileds on interleukin-1 beta and postoperative pain: a double-blind, placebo-controlled, pilot study in breast reduction patients; Plastic and Reconstructive Surgery; 125(6); pp. 1620-1629; Jun. 2010.
Ross et al.; Effect of time-varied magnetic field on inflammatory response in macrophage cell line RAW 264.7; Electromagnetic Biology and Medicine; 32(1); pp. 59-69; Mar. 2013.
Ross et al.; Effect of pulsed electromagnetic field on inflammatory pathway markers in RAW 264.7 murine macrophages; Journal of Inflammation Research; 6; pp. 45-51; (year of pub. sufficiently earlier than effective US filing date and any foreign priority date) 2013.
Selvam et al.; Low frequency and low intensity pulsed electromagnetic field exerts its antinflammatory effect through restoration of plasma membrane calcium; Life Sciences; 80(26); pp. 2403-2410; Jun. 6, 2007.
Serhan et al.; Anti-inflammatory and proresolving lipid mediators; Annu. Rev. Pathmechdis. Mech. Dis.; 3; pp. 279-312; 43 pages; (Author Manuscript); Feb. 28, 2008.
Serhan et al.; Maresins: novel macrophage mediators with potent anti-inflammatory and proresolving actions; Journal of Experimental Medicine; 206(1); pp. 15-23; Jan. 16, 2009.
Serhan et al.; Protectins and maresins: New pro-resolving families of mediators in acute inflammation and resolution bioactive metabolome; Biochimica et Bipphysics Acta (BBA)—Molecular and Cell Biology of Lipid; 1851(4); pp. 397-413; 40 pages; (Author Manuscript); Apr. 30, 2015.
Serhan; Novel lipid mediators and resolution mechanisms in acute inflammation: to resolve or not ?; The American Journal of Pathology; 177(4); pp. 1576-1591; Oct. 2010.

Serhan; Novel pro-resolving lipid mediators are leads for resolution physiology; Nature; 510(7503); pp. 92-101; 24 pages; (Author Manuscript); Jun. 2014.
Cho et al. ..; Discovery of (2-fluoro-benzyl)-(2-methyl-2 phenethyl-2H-chromen-6-yl)-amine (KRH-102140) as an orally active 5-lipoxygenase inhibitor with activity in murine inflammation models; Pharmacology; 87(1-2); pp. 49-55; Feb. 2011.
Spite et al.; Resovins, specialized proresolving lipid mediators, and their potential roles in metabolic diseases; Cell Metabolism; 19(1); pp. 21-36; Jan. 7, 2014.
Serhan et al.; Resolving inflammation: dual anti-inflammatory and pro resolution lipid mediators; Nature Reviews Immunology; 8(5); pp. 349-361; 31 pages; (Author Manuscript); May 2008.
Stein et al.; Peripheral mechanisms of pain and analgesia; Brain Research Reviews; 60(1); pp. 90-113; 38 pages; (Author Manuscript): Apr. 2009.
Suleyman et al.; Anti-inflammatory and side effects of cyclooxygenase inhibitors; Pharmacological Reports; 59(3); pp. 247-258; May 2007.
Uddin et al.; Resolvins: natural agonists for resolution of pulmonary inflammation; Progress in Lipid Research; 50(1); pp. 75-88; 30 pages; (Author Manuscript); Jan. 31, 2011.
Vilcek; The cytokines: an overview; in: Thomson WAaMTL, ed.; The Cytokine Handbook. 4 ed. San Diego: Academic Press, Calif, USA; pp. 1-18; (year of pub. sufficiently earlier than effective US filing date and any foreign priority date) 2012.
Wagener et al.; Different faces of the heme-heme oxygenase system in inflammation; Pharmacological Reviews; 55(3); pp. 551-571; Sep. 2003.
Wagener et al.; The heme-heme oxygenase system: a molecular switch in wound healing; Blood; 102(2); pp. 521-528; Jul. 15, 2003.
Wegiel et al.; Go green: the anti-inflammatory effects of biliverdin reductase; Frontiers in Pharmacology; 3; Article 47; doi: 10.3389/fphar.2012.00047; 8 pages; Mar. 16, 2012.
Xu et al.; Resolvins RvE1 and RvD1 attenuate inflammatory pain via central and peripheral actions; Nature Medicine; 16(5); pp. 591-597; 10 pages; (Author Manuscript); May 2010.
Yang et al.; Metabolomics-lipidomics of eicosanoids and docosanoids generated by phagocytes; Current Protocols in Immunology; 95(1); pp. 14-26; 36 pages; (Author Manuscript); Nov. 2011.
Yang et al.; Reactive oxygen species in the immune system; International Reviews of Immunology; 32(3); pp. 249-270; Jun. 2013.
Yeretssian et al; Molecular regulation of inflammation and cell death; Cytokine; 43(3); pp. 380-390; Sep. 2008.
Kirk et al.; U.S. Appl. No. 17/040,636 entitled "High-power pulsed electromagnetic field applicator systems," filed Sep. 23, 2020.
Elsiminger et al.; U.S. Appl. No. 17/829,915 entitled "Method and apparatus for treating pre-ulcerative lesions with pulsed electromagnetic fields," filed Jun. 1, 2022.
Ferrer Herrera et al.; U.S. Appl. No. 17/832,444 entitled "Patient authentication and remote monitoring for pulsed electromagnetic field systems," filed Jun. 3, 2022.

\* cited by examiner

CURRENT-BASED RF DRIVER FOR PULSED ELECTROMAGNETIC FIELD APPLICATOR SYSTEMS

CROSS REFERENCE TO RELATED APPLICATIONS

This application claims the benefit of U.S. Provisional Patent Application No. 62/926,375, filed Oct. 25, 2019, titled "CURRENT-BASED RF DRIVER FOR PULSED ELECTROMAGNETIC FIELD APPLICATOR SYSTEMS," which is herein incorporated by reference in its entirety.

The following U.S. patent applications are herein incorporated by reference in their entirety to the same extent as if each individual publication or patent application was specifically and individually indicated to be incorporated by reference: U.S. Pat. No. 6,334,069, titled "PULSED ELECTROMAGNETIC ENERGY TREATMENT APPARATUS AND METHOD", filed on Jan. 15, 1999, U.S. Pat. No. 6,353,763, titled "PULSED ELECTROMAGNETIC ENERGY TREATMENT APPARATUS AND METHOD", filed on Jun. 27, 2000, U.S. Pat. No. 6,967,281, titled "COVER FOR ELECTROMAGNETIC TREATMENT APPLICATOR", filed on Oct. 22, 2003, U.S. Pat. No. 6,974,961, titled "COVER FOR ELECTROMAGNETIC TREATMENT APPLICATOR", filed on Sep. 14, 2000, U.S. Pat. No. 7,024,239, titled "PULSED ELECTROMAGNETIC ENERGY TREATMENT APPARATUS AND METHOD", filed on Nov. 20, 2001, PCT Patent Application No. PCT/US2015/062232, titled "TREATMENT OF CONDITIONS SUSCEPTIBLE TO PULSED ELECTROMAGNETIC FIELD THERAPY", filed on Nov. 23, 2015, U.S. patent application Ser. No. 15/527,977 filed on May 18, 2017, entitled "TREATMENT OF CONDITIONS SUSCEPTIBLE TO PULSED ELECTROMAGNETIC FIELD THERAPY", PCT Application No. PCT/US2018/043358, filed Jul. 24, 2018, entitled "ELECTROMAGNETIC FIELD APPLICATION SYSTEM", PCT Application No. PCT/US2019/023860, filed Mar. 25, 2019, entitled "HIGH-POWER PULSED ELECTROMAGNETIC FIELD APPLICATOR SYSTEMS", and U.S. patent application Ser. No. 16/449,133, filed Jun. 21, 2019, entitled "HIGH-POWER PULSED ELECTROMAGNETIC FIELD APPLICATOR SYSTEMS."

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to pulsed electromagnetic field (PEMF) systems, apparatuses and methods. In particular, the disclosure relates to pulsed electromagnetic field (PEMF) applicator apparatuses having a single RF driver providing pulsed current-based signals to one or more applicators.

BACKGROUND

Pulsed electromagnetic fields (PEMF) have been described for treating therapeutically resistant problems of both the musculoskeletal system as well as soft tissues. PEMF typically includes the use of low-energy, time-varying magnetic fields. For example, PEMF therapy has been used to treat non-union bone fractures and delayed union bone fractures. PEMF therapy has also been used for treatment of corresponding types of body soft tissue injuries including chronic refractory tendinitis, decubitus ulcers and ligament, tendon injuries, osteoporosis, and Charcot foot. During PEMF therapy, an electromagnetic transducer coil is generally placed in the vicinity of the injury (sometimes referred to as the "target area") such that pulsing the transducer coil will produce an applied or driving field that penetrates to the underlying tissue.

Treatment devices emitting magnetic and/or electromagnetic energy offer significant advantages over other types of electrical stimulators because magnetic and electromagnetic energy can be applied externally through clothing and wound dressings, thereby rendering such treatments completely non-invasive. Moreover, published reports of double blind placebo-controlled clinical trials utilizing a RF transmission device (Diapulse) suggest that this ancillary treatment device significantly reduces wound healing time for chronic pressure ulcers as well as for surgical wounds. Studies using Dermagen, a magnetic device manufactured in Europe which produces a low frequency magnetic field, have demonstrated significant augmentation of healing of venous stasis ulcers. Additionally, it has been shown for groups of patients treated with electromagnetic energy, that 50% fewer patients of that treatment group develop reoccurring pressure ulcers, compared to control patients, suggesting that electromagnetic energy treatments impart some resistance to the reoccurrence of chronic wounds, such as pressure ulcers. Electromagnetic energy may also be useful as a preventative strategy. Analysis of the effects of electromagnetic energy on the treatment of pressure ulcers show that this treatment, by reducing healing time by an average of 50%, results in significant reductions in the costs associated with wound management.

Most PEMF transducers use a substantial amount of energy, and typically generate this energy in a base or controller portion, which may include batteries and/or a connection to a wall power source. The energy is typically conditioned or modulated into an appropriate power (e.g., voltage) signal and then transmitted (e.g., via a cable) to an applicator. Monitoring and controlling the amount of power received at the applicator for high-power apparatuses (e.g., apparatuses that deliver over 40 W or greater than 100 V or energy) typically requires feedback sensors at the applicator itself. This, amongst other reasons, may make the apparatuses expensive, and in some variations, heavy. Patient comfort while using such devices is often inversely proportional to the weight.

SUMMARY OF THE DISCLOSURE

In general, described herein are pulsed electromagnetic field (PEMF) apparatuses (e.g., devices and systems) including a controller configured to generate a pulsed current signal; and one or more applicators coupled to the controller, each applicator comprising a coil circuit configured to receive the pulsed current signal and to emit a PEMF signal comprising a magnetic field signal. In particular, apparatuses are described herein that are configured to operate one, and in some variations, more than one applicator from a single controller by multiplexing signal or by simultaneously delivering signal to more than one applicator, e.g., a plurality of applicators.

Described herein are single radio frequency (RF) driver current-based PEMF applicator apparatuses that may reduce device complexity and may increase treatment efficiency. For example, the apparatuses described herein may transmit a controlled current, which may be advantageously monitored at the RF driver, permitting simplification of the apparatus requirements. Further, the apparatuses and methods described herein may regulate the application of the magnetic (H) field or the ratio of the H field to E field to provide enhanced outcomes.

Described herein are pulsed electromagnetic field (PEMF) applicator apparatuses which may include a controller configured to generate a pulsed current signal; and one or more applicators coupled to the controller, each applicator having a coil circuit configured to receive the pulsed current signal and to emit a PEMF signal comprising a magnetic field signal.

In general, these apparatuses and methods may be current based, rather than voltage-based which may allow them to reduce or eliminate the need for feedback sensors. For example the apparatuses described herein may reliably control the applied energy (and particularly the magnetic field applied) without the need for a feedback sensor at the applicator. This is because these apparatuses may be configures so that the current will be the same at the driver as at the applicator(s). Thus, the feedback control can be integrated with the driver (e.g., separate from the applicator). The driver, unlike previously described PEMF drivers, is current, rather than voltage based. By using current, rather than voltage, the components (e.g., applicators, driver, etc.) can be connected serially. The current outputted by the driver may be identically output by each applicator, allowing monitoring of the current at the driver side and control of the current at the driver side, without requiring monitoring of current at the applicator.

In general, in the apparatuses described herein, the magnetic field generated by the applicator is proportional to the current. Thus, for example, monitoring the current may allow monitoring the applied H-field. In some variations a separate H-field sensor may be included at one or more of the applicators.

The magnetic field applied may penetrate the body (e.g., whereas the majority of the electric field may be reflected from the surface of the body). The magnetic field may therefore be the applied dose, delivered to the target tissue (e.g., cells). Although there will be an associated electric filed, it may play a minor role (e.g., may be the result of an eddy current from the applied magnetic field).

For example, in some variations the apparatuses described herein may provide a magnetic field strength of approximately 5-500 A/m (e.g., between 5-10 A/m, between 18-31 A/m, between 20-40 A/m, between 25-50 A/m, between 60-80 A/m, between 60-200 A/m, between 100-200 A/m, between 100-500 A/m, between 200-500 A/m, etc.). In some variations the apparatus is configured to deliver a magnetic field having a field strength that is approximately 30 A/m (e.g., +/−20 A/m), 75 A/m (e.g., +/−20 A/m), 175 A/m (e.g., +/−20 A/m), etc. In some variations a magnetic field sensor in the applicator may confirm what is being measured. In some variations the minimum current density applied by the apparatus may be, e.g., between 20 A/m, and the maximum may be up to 500 A/m. As mentioned above, in some variations the apparatus may be configured to limit the applied electric field (using shielding, such as electrostatic shielding) so that a much larger magnetic field is applied, relative to the electric field.

In some variations the apparatus may include an electrostatic shield around the current radiator (in the applicator), which may create a constant capacitance. The impedance may change substantially based on what body part the field is being applied to (e.g., foot, hand, etc.), because of the capacitance in the applied electric field. The human body is grounded—changes its impedance near the applicator. The electrostatic shielding may prevent capacitance changes based on the target, maintaining the impedance of the applicator. The electrostatic shielding may be configured to provide a consistent impedance matching (e.g., of 50 ohms). This may allow impedance matching with other components of the apparatus (e.g., the board driving the applicator, the applicator, etc.) which may allow the maximum transfer of power to the radiator (applicator), minimizing loss due to reflection. For example, the electrostatic shielding may modify the electric field without proportionally effecting the magnetic field. Bringing the applicator towards a human body part (e.g., a hand) may establish a capacitance between the hand and the applicator. To protect against this, an electrostatic shield may be included just for the e-field applied (which may be substantially transparent to the magnetic field applied). The electrostatic shielding may therefore attenuate the electric field, but not substantially attenuate the magnetic field.

As mentioned above, in any of these apparatuses and methods the applicator may not include a sensor that feeds back to the driver/controller. For example, the magnetic field may be directly controlled by the current (reducing or eliminating the need to send a signal from the applicator to control the applied magnetic field). The closed-loop feedback may maintain a constant magnetic field, without requiring a sensor at the applicator.

In some variations, the method and apparatuses described herein may also include single RF board (driver) that may drive multiple applicators. The driver may be configured to include a series switch or path transistor that switches (e.g., turns on/off) the system rapidly, e.g., providing an "on" time of between 20 μsec and 1000 μsec, e.g., between 20 μsec and 100 μsec, between 30 μsec and 50 μsec, e.g., approximately 42 μsec) and applying pulses for milliseconds (e.g., x ms, where x is between 1-1000). For example, the driver may be configured to deliver 42 μsec pulses every 1 ms (e.g., having an approximately 4.2% duty cycle). The driver may provide current pulses to the applicators which each include one or more coils. The driver may therefore include a current sensor that provides feedback to the driver (e.g., power supply). In some variations the current sensor (or any additional current sensors) may be included at the applicator. The current sensor may be used as feedback to regulate the applied magnetic field; the applied magnetic field may be related to the current, as well as the geometry and/or dimensions of the coil on the applicator (e.g., the H-field may be proportional to number of turns, and inversely proportional to radius of coil, as well as the applied current). Thus, the apparatus may control the applied H-field based on the current and geometry of the applicator/coil.

In some variations, the switch used for the driver may be driven by a low-voltage pulse (e.g., a relay configured to handle high current by low voltage control, where the high current may be hundreds of Amps or more).

The apparatuses described herein may generally include cabling connecting the applicator to the driver. For example, in some variations the cabling may include twisted pairs of cables. In some variations the cabling may be coaxial; the coaxial cabling may also be twisted. In some variation only a single coaxial cable is needed, as the RF energy may be delivered by the single cable and RF feedback may not be necessary (e.g., no RF return). In variations in which multiple applicators are used, each application may be connected to the driver by a separate (and single) coaxial cable. In some variations the applicator(s) may be configured as smart applicators that include circuitry configured to allow it to be independently controlled.

As mentioned above, the controller may include a sensor configured to sense the pulsed current signal. As described in greater detail below, the controller may be configured to maintain the pulsed current signal at a selected current based on feedback from the current sensor. In some variations, the controller may further include a wireless remote controller.

The apparatus may include a composite cable connecting the controller with the one or more applicators. In some variations, the apparatus may further include a solid state multiplexer (MUX) circuitry configured to provide digital signals to the one or more applicators. In some variations, the solid state MUX circuitry may be disposed within one of the one or more applicators. Alternatively, the solid state MUX circuitry may be disposed generally between the controller and the one or more applicators.

As mentioned, in some variations, the coil circuit of each of the one or more applicators may further comprise an electrostatic shield about the coil circuit. For example, the PEMF signal at each of the one or more applicators may have an electrical field signal that is from 5% to 80% (e.g., between 5% and 75%, between 5% and 60%, between 5% and 50%, between 10% and 80%, between 20% and 80%, between 30% and 80%, between 40% and 80%, etc.) of the magnetic field signal.

In some variations, at least one of the one or more applicators may further include an indicator device energized by magnetic induction from the coil circuit. The indicator device may be an LED or a vibrator device. In some variations, the controller may further include an RFID reader and each of the one or more applicators comprises a unique RFID signal. The unique RFID signal of each of the one or more applicators may be configured to identify a specific application for the applicator. In some variations, the unique RFID signal may be configured to instruct the controller to provide a selected pulsed current signal, wherein the selected pulsed current signal comprises a pre-selected current signal, a pre-selected pulse duration, a pre-selected pulse frequency, or a combination thereof.

Each of the one or more applicators may be configured to emit the PEMF signal without interference from any other of the one or more applicators. In some variations, each of the one or more applicators may be configured to provide an electromagnetic field having a magnetic field strength (H), e.g., between 10 to 500 A/m. For example, each of the one or more applicators may be configured to provide an electromagnetic field having a magnetic field strength (H) between 15 to 40 A/m, between 18 to 31 A/m, between 40-100 A/m, between 50-200 A/m, between 200-500 A/m, etc. In some other variations, the apparatus may be configured to provide an electromagnetic field having a magnetic field strength (H) between 60 to 80 A/m.

Any appropriate PEMF signal may be applied. For example, the current-based pulsed electromagnetic field signal may have a carrier frequency in the MHz range. For example, the carrier frequency may be between about 6 MHz and 100 MHz (e.g., about 27 MHz, about 10 MHz, between about 10 MHz and 60 MHz, etc.). The pulsed electromagnetic field signal may have a pulse width of between about 1 microsecond and about 200 microseconds.

In another aspect, a pulsed electromagnetic field (PEMF) apparatus for one or more applicators is provided, including a controller including a MUX circuitry, the controller configured to generate a pulsed current signal; and one or more applicators coupled to the controller, each applicator comprising a coil circuit configured to receive the pulsed current signal and to emit a PEMF signal comprising a magnetic field signal.

The controller may include a sensor configured to sense the pulsed current signal. As described in greater detail below, the controller may be configured to maintain the pulsed current signal at a selected current based on feedback from the current sensor. In some variations, the controller may further include a wireless remote controller.

In some variations, the apparatus may further include at least two applicators, wherein the at least two applicators are connected in series with the controller. Alternatively, the apparatus may further include at least two applicators, where the at least two applicators are connected in parallel with the single current-based RF energy driver. Each of the at least two applicators may be configured to emit the PEMF signal without interference from the other of the at least two applicators.

In some variations, the coil circuit of each of the one or more applicators may further comprise an electrostatic shield about the coil circuit. The PEMF signal at each of the one or more applicators may have an electrical field signal that is attenuated (e.g., by 10% or more, 20% or more, 30% or more, 40% or more 50% or more, 60% or more, 70% or more, 75% or more, 80% or more, etc.) as compared to the magnetic field signal.

In some variations, at least one of the one or more applicators may further include an indicator device energized by magnetic induction from the coil circuit. The indicator device may be an LED or a vibrator device. In some variations, the controller may further include an RFID reader and each of the one or more applicators comprises a unique RFID signal. The unique RFID signal of each of the one or more applicators may be configured to identify a specific application for the applicator. In some variations, the unique RFID signal may be configured to instruct the controller to provide a selected pulsed current signal, wherein the selected pulsed current signal comprises a pre-selected current signal, a pre-selected pulse duration, a pre-selected pulse frequency, or a combination thereof.

Each of the one or more applicators may be configured to emit the PEMF signal without interference from any other of the one or more applicators. In some variations, each of the one or more applicators may be configured to provide an electromagnetic field having a magnetic field strength (H) between 10 to 200 A/m. Alternatively, each of the one or more applicators may be configured to provide an electromagnetic field having a magnetic field strength (H) between 15 to 40 A/m or between 18 to 31 A/m. In some other variations, the apparatus may be configured to provide an electromagnetic field having a magnetic field strength (H) between 60 to 80 A/m.

Any appropriate PEMF signal may be applied. For example, the current-based pulsed electromagnetic field signal may have a carrier frequency in the MHz range. For example, the carrier frequency may be between about 6 MHz and 100 MHz (e.g., about 27 MHz, about 10 MHz, between about 10 MHz and 60 MHz, etc.). The pulsed electromagnetic field signal may have a pulse width of between about 1 microsecond and about 200 microseconds.

In another aspect, a method of controlling operation of a pulsed electromagnetic field (PEMF) apparatus for one or more applicators is provided, including transmitting a pulsed current signal from a controller to the one or more applicators; and emitting a PEMF signal comprising a magnetic field signal from at least one of the one or more applicators.

In some variations, the method may further include sensing the pulsed current signal at the controller. The method may further maintaining the pulsed current signal at a selected current. In some variations, maintaining the pulsed current signal at the selected current may be based on sensing the pulsed current signal at the controller.

In some variations, the method may further include electrostatically shielding a coil circuit of the one or more applicators thereby reducing an electrical field signal of the PEMF signal. Electrostatically shielding the coil circuit of the one or more applicators may reduce the electrical field signal more than the magnetic field signal of the PEMF signal. In some variations, an electrical field signal of the PEMF signal may be 10% to 30% of the magnetic field signal.

In some variations, the method may further include transmitting the pulsed current signal to each of the one or more applicators substantially simultaneously. Alternatively, the method may further include transmitting the pulsed current signal to each of the one or more applicators sequentially, such that the pulsed current signal is transmitted to only one of the one or more applicators at a time.

In some variations, the method may further include detecting an indicator signal from at least one of the one or more applicators. The indicator signal may be a visible or a vibratory signal indicating that the at least one of the one or more applicators is emitting the pulsed magnetic field signal.

The current-driven pulsed electromagnetic field (PEMF) apparatus having a single RF Driver/Controller and one or more applicators for use in the method may include any components and may be configured in any combination as described herein.

In another aspect, a method of operating a pulsed electromagnetic field (PEMF) apparatus for one or more applicators is provided, including detecting an identifier from each of the one or more applicators; selecting a protocol compatible with the identifier of the one or more applicators; transmitting a pulsed current signal from a controller to the one or more applicators; and emitting a PEMF signal comprising a magnetic field signal from at least one of the one or more applicators. The identifier may be an RFID signal.

In some variations, the identifier may identify a specific application for each applicator, e.g., a body part for which the applicator may be specifically designed to treat. In some variations, detecting the RFID identifier may further include instructing the controller to provide a selected pulsed current signal, wherein the selected pulsed current signal may include a pre-selected current signal, a pre-selected pulse duration, a pre-selected pulse frequency, or a combination thereof. The current-driven pulsed electromagnetic field (PEMF) apparatus having a single RF Driver/Controller and one or more applicators for use in the method may include any components and may be configured in any combination as described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
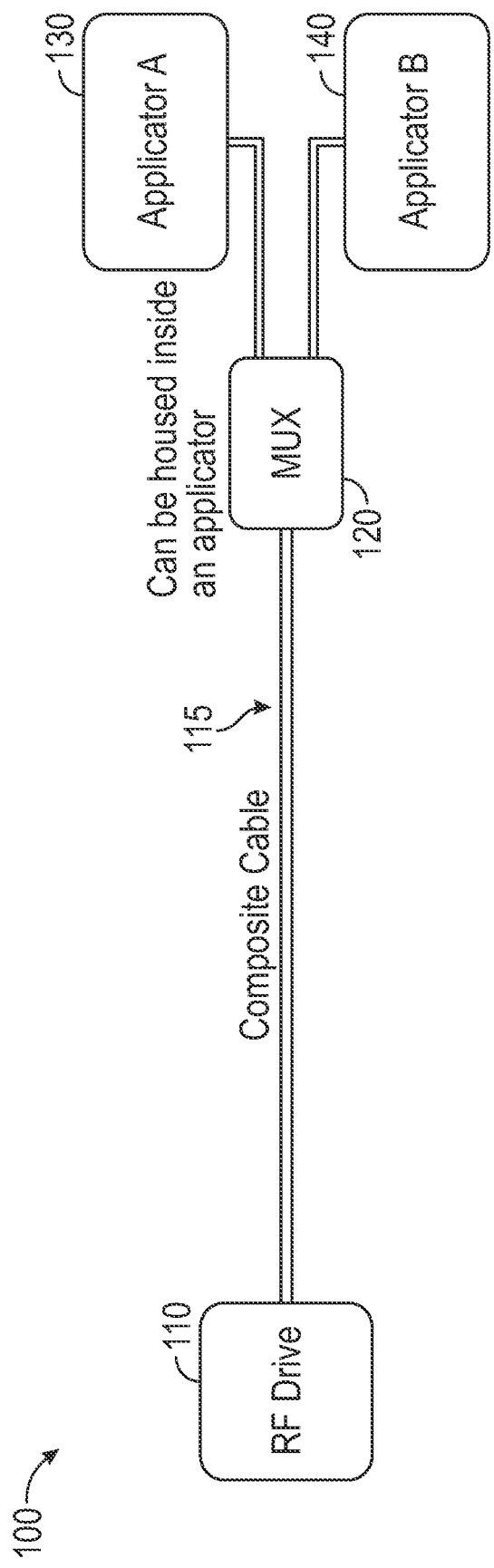
FIG. 1A is a schematic representation of a current-based RF driver for a PEMF applicator apparatus according to some variations of the disclosure.

Current apparatuses in the field of EM treatment generally uses an energy source (e.g., a RF Driver) for each applicator in the system. Building and assembly of the multiple RF drive boards introduces inconsistencies in the radiated treatment fields emitted from these applicators. This also increases cost and size of the systems. Additionally, the typical multiplicity of cabling in the commercially available apparatuses is awkward to use. Therefore, there is a need in the field for improved PEMF applicator apparatuses for more compliant and convenient use, reducing complexity and weight and increasing the margin of safety of the energetics.

Apparatuses are described herein that reduce the number of energy Drives to only one current-driven Driver (which may be a RF Driver, but the apparatus is not so limited), regardless of the number of treatment applicators, which may be one or more applicators. The apparatuses thus configured can more simply control the electronics to provide the energetics as pulsed current signals to the one or more applicators. This provides more consistent control of PEMF treatment Energy radiated from the one or more applicators, as described more fully below. In some variations, the feedback sensor, which for these apparatuses is a current sensor, may be disposed within or adjacent to the controller. This reduces complexity and weight by removing the requirement for power sensing at each of the one or more applicators including radiator coils. The cabling requirements between the single Driver/Controller for current-driven apparatuses can be achieved with a greater number of alternative configurations and with less expensive components. Additionally, the current-based Driver (e.g., RF, which may be AC or DC) apparatus may be configured to provide greater insensitivity to the proximity and variability of capacitive properties of the subject's body. Each advantage described, taken singly or in any combination, can offer PEMF applicator apparatuses affording more consistent treatment, more deeply/more specifically/more powerfully targeted treatment, and/or increased ease of deployment for the subject's use.

A pulsed electromagnetic field (PEMF) apparatus for one or more applicators includes a controller (e.g., a RF Driver/Controller) configured to generate a pulsed current signal; and one or more applicators coupled to the controller, where each applicator includes a coil circuit configured to receive the pulsed current signal and to emit a PEMF signal comprising a magnetic field signal. This current-based apparatus advantageously employs a single Driver/Controller (e.g., RF Driver) which can provide the same current to each of the one or more applicators, as shown in any of FIGS. 1A-4. Since the H-field is directly proportional to current, the RF drive controller consists of a constant current source and a current sensor. The current through every applicator/radiator is well stabilized by the closed loop current feedback process. By using current rather than voltage to drive the radiation of the EMF fields from the coils of the applicator(s), applicator(s) may be connected in series or in parallel with the single RF Driver/Controller. Since the pulsed current signal that the Driver outputs is the same to each of the one or more applicators, the current may be monitored at the Driver side of the system. The current does not need to be sensed at each of the applicators, unlike the voltage monitoring required in a voltage-driven system. Similarly, the current can be controlled at the Driver side of the apparatus the control may be based on the feedback from the current sensor at the Driver side of the system. Therefore, the apparatus is less complex, and less costly to build.

Another advantage to the single Driver current-based apparatus is that the electrical current sensed by the sensor is directly proportional to the magnetic field that the applicator(s) produce. The magnetic field is the component of the EMF generated by the radiating coil of the applicator(s) that produces the therapeutic effect within the subject's body, as the electrical field does not penetrate much beyond the first centimeter or so of the surface being treated. Much of the electrical field is reflected, and therefore does not contribute to the therapeutic effect. In contrast, the magnetic field is the EMF component that can penetrate to depth, producing eddy currents which provide the physiological stimulating effect to accelerate nerve or bone healing.

The single current-based driver may be a RF Driver, The RF Driver may have a carrier frequency of 27.12 MHz or a harmonic thereof (e.g., a frequency of 13.56 MHz). In another variation, there may be no carrier frequency. The energy source may be a wall source and/or batteries.

Figure 2:
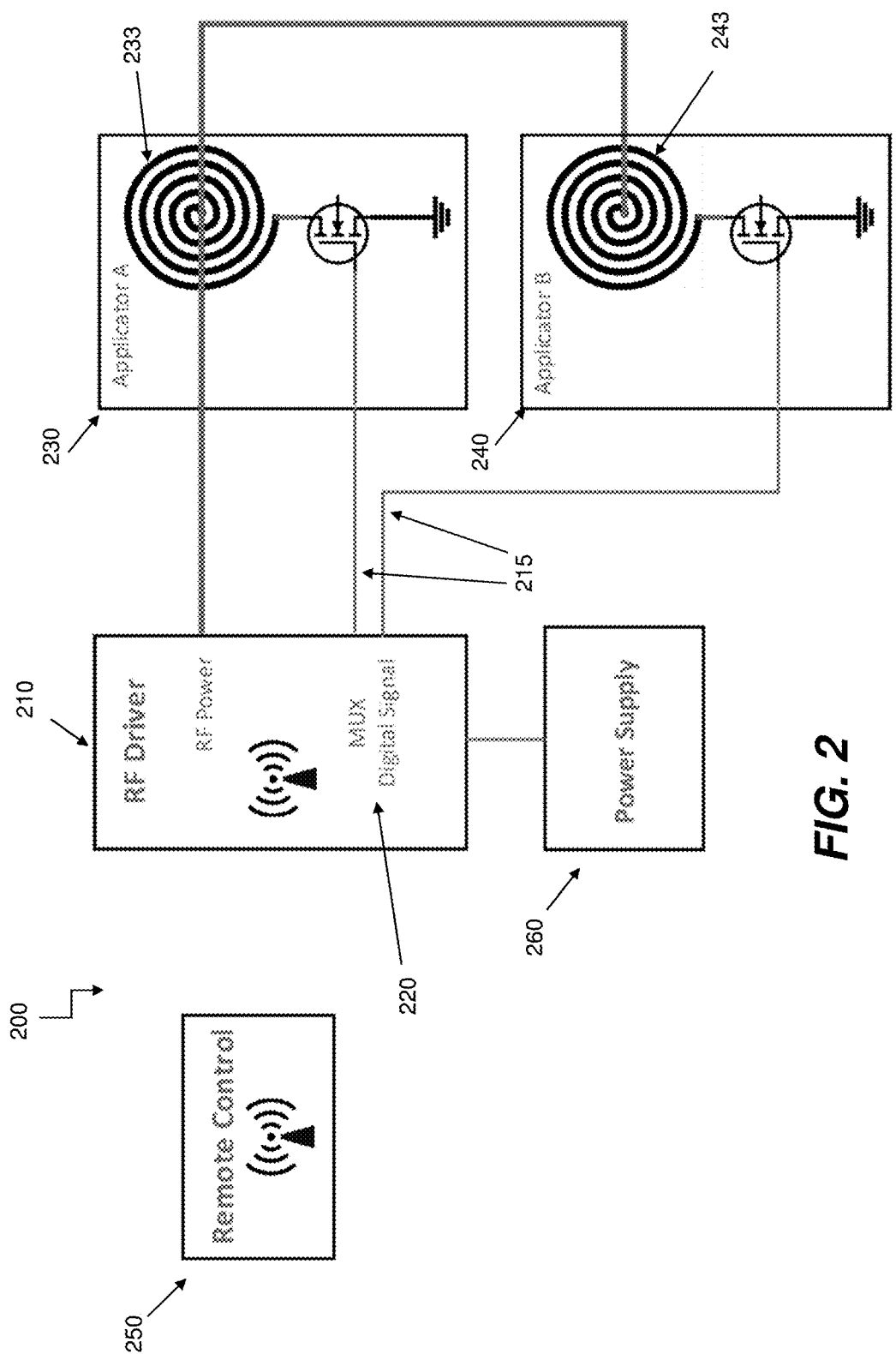
FIG. 2 is a schematic representation of a single current-based RF driver for a PEMF applicator apparatus according to some variations of the disclosure.

Driver and Applicator connectivity options. A composite cable may be used to connect the Driver/Controller with the one or more applicators, which may be configured in several different options. In some variations, a solid state MUX circuitry may be included in the apparatus to provide digital signals to the one or more applicators. The solid state MUX circuitry may be disposed as a separate component connecting the Driver/Controller with the one or more applicators, as shown in FIG. 1A, or it may be disposed within one of the one or more applicators (not shown). In some other variations, the Driver/Controller may include a MUX circuitry, replacing a RF Drive circuitry as shown in FIG. 2. In some variations, the one or more applicators may be connected in series or in parallel with the Driver/Controller. In some variations, at least two applicators are connected in series (FIG. 3) or parallel with the Driver/Controller. In some other variations, more than two applicators are connected in series or in parallel with the Driver/Controller. In some variations, an optional H-field sensor may be disposed within each applicator to confirm the measurement of the magnetic field generated.

Applicators. An applicator for use in the PEMF apparatuses and methods described herein, include a coil circuit configured to receive the pulsed current signal and to emit a PEMF signal comprising a magnetic field signal. When more than one applicators are present in the system, each of the more than one applicators emits the EMF signal without interference from the other of the more than one applicators.

The applicator(s) of the single current-based Driver PEMF apparatus may provide a magnetic field having a magnetic field strength (H) between about 10 A/m to about 200 A/m; about 15 A/m to about 150 A/m; about 20 A/m to about 125 A/m; about 30 A/m to about 100 A/m; about 40 A/m to about 90 A/m, about 60 A/m to about 80 A/m, about 75 A/m to about 90 A/m, or any selected value of magnetic field strength within this recitation. In some variations, applicator(s) of the single current-based Driver PEMF apparatus may provide a magnetic field having a magnetic field strength (H) between about 15 to about 40 A/m, between about 18 to about 31 A/m, between about 60 A/m to about 80 A/m, or about 30 A/m, about 75 A/m, about 150 A/m, or about 175 A/m.

Impedance matching and control. In some variations, the apparatuses described herein may be configured (tuned) to operate at one or more specific load configurations. These load configurations may adjust parameters within the base unit and/or applicator. The base unit and/or applicator(s) may be configured to switch (manually and/or automatically) between different load configurations. For example, the base unit and/or applicator may be configured to apply the high-energy PEMF (and particularly high magnetic field energy) to a specific body part (e.g., a subject's foot, arm, knee, hand, torso, lower back, a head, a chest, leg, etc.). Thus, although the apparatuses described herein may trade off load sensitivity with compact and lightweight features, this tradeoff may be ameliorated by setting and/or switching between load parameters. For example, an applicator may be specifically tuned for use on a human foot. Thus, in this configuration, the load range may be set within a predefined range. The range may be set empirically, and may be set (via hardware/firmware, etc.) or switched from a look-up table. The range may be determined initially be sampling a population of people to determined expected loads on that body part.

In some variations of the apparatuses and methods described herein, the applicator may be configured with a helical antenna coil, rather than a uniform spiral coil. In some variations the helical coil comprises a trace that spirals around itself but changes diameter, getting wider as it circles outward. This spiral may be, in some variations, a logarithmic spiral. In some variation the space between the adjacent lines of the spiraling trace is constant while the thickness of the trace increases. In some variations the spacing between the adjacent lines of the trace varies. Thus, in any of the apparatuses described herein the applicator antenna coil may be a helical coil in which the coil starts thinner in middle and gets bigger as you circle out. This configuration may minimize the effect of the loading on the applicator.

In some configurations the load configurations of the applicator is adapted to be used with a particular body part. For example, the applicator may be configured to be applied specifically to a foot, hand, head, neck, arm, wrist, leg, torso, knee, etc.

For example, in some variations the applicator is configured to have a load that is adapted to be approximately 50 ohms, so that, when driven by the base unit, the applicator sees a load of about 50 ohm real and 0 imaginary; specifically, the cable connecting the applicator to the base unit should see about 50 ohms real and 0 imaginary. The load characteristics of the applicator may be configured so that the applicator is tuned to the expected load. If the applicator is applied to the wrong load (e.g., to a different body part), then then the apparatus may indicate that the applicator is not in contact with the correct body part. For example, the applicator may indicate that no load (if in air) or that an incorrect body part (e.g., "not the foot") than the body part for which the load was tuned in the applicator (e.g., an applicator, etc.).

In general, any of the apparatuses described herein may be configured to monitor the load seen by the applicator. This may be accomplished by measuring field strength. The sensed field strength may be used to set the drive level. If the applicator is applied outside of the select range, the apparatus may give a feedback error. For example, if the apparatus sees the wrong load (e.g., when an applicator tuned for a foot is applied to a lower back, for example), the load is mismatched, and the efficiency of the field will be outside of a predicted range, which may result in the apparatus indicating an error. Thus, the apparatus may, but does not need to specifically measure the load, but may instead use the field strength. If the load is mismatched, the field strength will be outside of the expected range and the apparatus may have to drive harder to try and achieve the target field strength. This may therefore result in an error, as described above, including an indication that the applicator is being applied to the incorrect body region (or is in air). This message may be presented to the user (e.g., on the output of the base unit) and/or may be stored and/or transmitted, and may be used for patient monitoring (e.g., compliance monitoring). For example, if there is a no-load condition on the apparatus, the apparatus may determine if the device is actually being used (or is in air), or is being used correctly. This may indicate compliance information.

Figure 5:
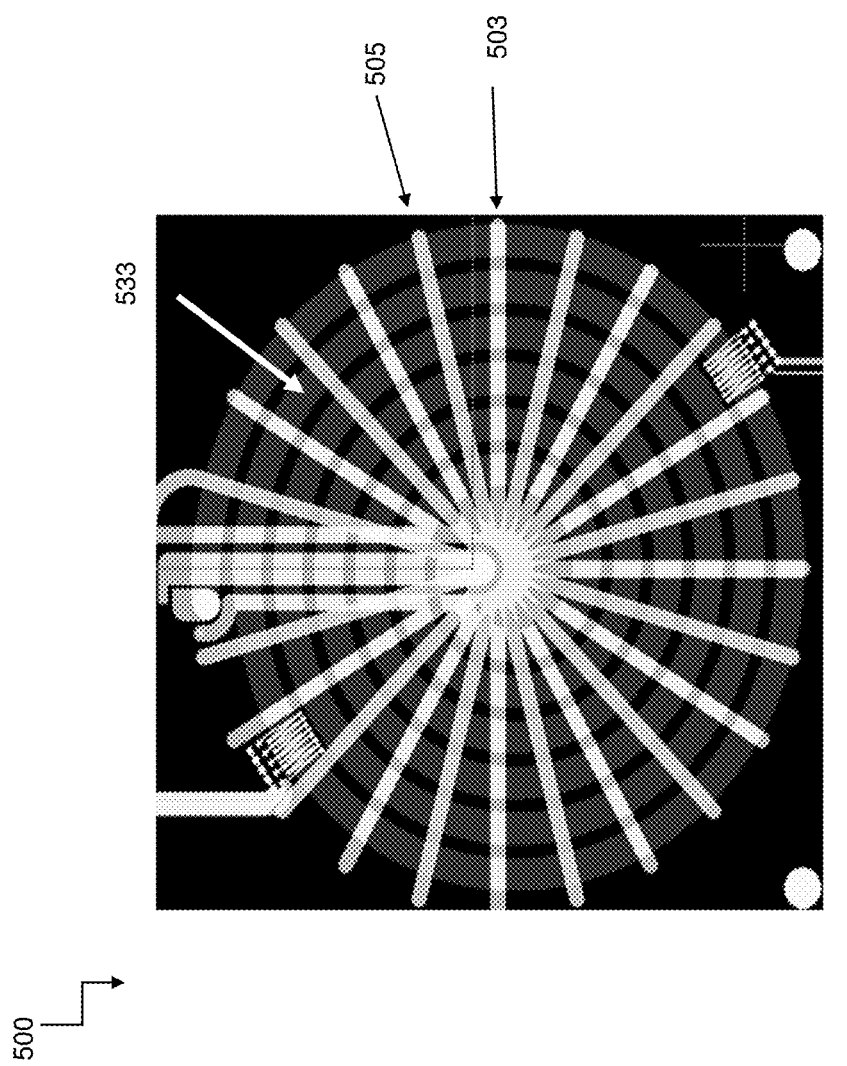
FIG. 5 is a schematic representation of electrostatic shielding for the coil circuit of an applicator according to some variations of the disclosure.

Electrostatic shielding. In some variations, the coil circuit of each of the one or more applicators may further include an electrostatic shield about the coil circuit. This may be used in the current-driven PEMF apparatus described herein or may be used in any voltage-driven PEMF system. When the electrostatic shield is disposed about both sides of the coil, as shown in FIG. 5, the emitted electric field is dissipated, while not affecting the emitted magnetic field. Electrostatic shielding may prevent impedance change as the applicator is brought close to or in contact with a body part of the subject. The shielding creates a capacitance that is constant, no matter how the applicator is brought close to the subject's body.

The electrostatic shield disposed about the coil circuit of the applicator may modify the electric field signal of the emitted PEMF signal such that each of the one or more applicators emits an electrical field signal that is about 10%, about 20%, about 30%, about 40%, or about 50% of the magnetic field signal. In some embodiments, the electric field of the emitted PEMF signal from each of the one or more applicators may less than about 30%, less than about 20%, less than about 15%, less than about 10%, less than about 9%, less than about 8%, less than about 5%, less than about 1% of the emitted magnetic field.

Applicator Operator Indicator. In some variations, at least one of the one or more applicators further includes an indicator device energized by magnetic induction from the coil circuit. The indicator device may include an LED or a vibrator device.

RFID identification of applicator class. In some variations, the controller may further include an RFID reader and each of the one or more applicators may include a unique RFID tag/signal. The unique RFID signal of each of the one or more applicators may be configured to identify a specific application, e.g. use at a specific body part, for the applicator. In some variations, the unique RFID signal may be configured to instruct the controller to provide a selected pulsed current signal, wherein the selected pulsed current signal may include a pre-selected current signal, a pre-selected pulse duration, a pre-selected pulse frequency, or a combination thereof.

Pulse width and duty cycles. In some variations, the pulsed electromagnetic field signal may have a pulse width of between about 1 microsecond to about 200 microseconds, or any value therebetween, and may have a repeat cycle of about 0.01 msec to about 10 msec, or any value therebetween.

Depending the configuration of the PEMF system, the applicators may receive current-based signals in a time wise multiplexed fashion, which may be performed in any suitable pattern. In some variations, the more than one applicators may receive current-based signals simultaneously.

The PEMF apparatus may include a switch to control the on/off of the current pulse signal. The switch may be driven by a low-voltage pulse, e.g., a relay or the like.

Communications circuitry. Any of the single current-based RF driver containing electromagnetic field (PEMF) applicator apparatuses described herein may be configured for wireless connectivity. In such connectivity, as shown in FIG. 2, the apparatus may include a remote controller. A subject or a caregiver may control the current-driven PEMF applicators of the apparatus to initiate, modulate or cease the operation of applicators. The remote control of operation of the current driven PEMF applicator apparatus may access one or more therapeutic modules for execution, which may be stored locally or remotely in a database, e.g. as part of a subscription or prescription application in a web-based application.

In some variations, the apparatuses described herein may further be configured to include or operate with a cellular link that provides the capability to transmit compliance data (e.g., date, time, and applicator loading) for each user treatment, and/or device diagnostic data (e.g., status of power levels, display module, RFID module, memory, base unit temperature, etc.) to a remote processor, including a cloud data system. In addition to compliance monitoring, this apparatus may allow for remote troubleshooting and error correction. The wireless (e.g., cellular) link may also allow for electronic message delivery to the client and downloading of software updates when needed. In some variations patient-specific prescriptions can be delivered wirelessly (e.g., through the cellular link) to the apparatus.

The apparatuses described herein may be small and lightweight. In general, these apparatuses may include an embedded processor that can execute instructions and/or operate via wireless connection (e.g., cellular connection) to increase data storage and processing power, and may increase the efficiency, features and capabilities.

In some variations, the apparatus is configured to transmit information about the most recent prior use(s) upon activation (turning on) of the apparatus. For example, when the apparatus is turned on, use data (including, but not limited to compliance feedback) may be transmitted. This may allow the apparatus to adjust the next treatment (e.g., how the user is using it) based on the prior treatment data. This configuration may also provide diagnostic data, which may be used to indicate that the unit is functioning properly. For example, if the prior use data indicates that the unit is compromised, it may indicate that it should be replaced, and may be replaced immediately and/or may transmit information to the party responsible for maintaining the unit to replace or service it. In some variations the unit may present a message or messages to the user, either via the screen on the unit, or by calling or messaging (e.g., text messaging) the user with feedback, such as instructions to call the servicing party (including contact information for the servicing party).

In any of these apparatuses, the device may be configured to transmit the prior session at the start of the next treatment and may suspend or prevent the start of treatment until the data has either been transmitted or until at least some minimum number of attempts (e.g., 2 attempts, 3 attempts, 4 attempts, etc.) have been made, before the apparatus is released to allow treatment. Failed attempts may be collected and transmitted together later, including at the next power-up or prior to powering down.

In some variations, the apparatus may be operated using a prescription service. When a prescription service is used, the unit may configured to permit delivery of a certain (predetermined) number of treatments per prescription, or a number of daily treatments for a predetermined number of days. The apparatus (e.g., controller) may be configured to display and/or otherwise indicate to the under the number of treatment days/times left, and may also be configured to indicate that the user should contact their physician or health care provider to modify or extend a prescription.

The apparatuses described herein may also be configured to automatically receive, via the wireless circuitry, software upgrades Methods. The current-driven pulsed electromagnetic field (PEMF) apparatus having a single RF Driver/Controller may control the operation of one or more applicators by transmitting a pulsed current signal from the controller to the one or more applicators; and emitting a PEMF signal including a magnetic field signal from at least one of the one or more applicators. In some variations, controlling the operation of the one or more applicators may further include sensing the pulsed current signal at the controller. Further, the pulsed current signal may be maintained at a selected current. Optionally, maintaining the pulsed current signal may be performed based on the results of sensing the pulsed current signal. The current-driven pulsed electromagnetic field (PEMF) apparatus having a single RF Driver/Controller and one or more applicators may include any components and may be configured in any combination as described herein.

Controlling the operation of the one or more applicators may further include electrostatically shielding a coil circuit of the one or more applicators thereby reducing an electrical field signal of the PEMF signal. Electrostatically shielding the coil circuit of the one or more applicators can reduce the electrical field signal more than the magnetic field signal of the PEMF signal. The electrical field signal of the PEMF signal emitted by the one or more applicators may be reduced to be about 10%, about 20%, about 30%, about 40%, or about 50% of the magnetic field signal. In some embodiments, the electric field of the emitted PEMF signal from each of the one or more applicators may less than about 30%, less than about 20%, less than about 15%, less than about 10%, less than about 9%, less than about 8%, less than about 5%, less than about 1% of the emitted magnetic field.

In some variations, the pulsed current signal may be transmitted to each of the one or more applicators substantially simultaneously. Alternatively, the pulsed current signal may be transmitted to each of the one or more applicators sequentially, such that the pulsed current signal is transmitted to only one of the one or more applicators at a time.

In some variations, operating the one or more applicators may further include detecting an indicator signal from at least one of the one or more applicators. The indicator signal may be a visible or a vibratory signal indicating that the at least one of the one or more applicators is emitting a pulsed magnetic field signal.

In another aspect, operating a current-driven pulsed electromagnetic field (PEMF) apparatus having a single RF Driver/Controller and one or more applicators may include detecting an identifier from each of the one or more applicators; selecting a protocol compatible with the identifier of the one or more applicators; transmitting a pulsed current signal from a controller to the one or more applicators; and emitting a PEMF signal comprising a magnetic field signal from at least one of the one or more applicators. In some variations, the identifier may be a RFID tag/signal disposed on the at least one of the one or more applicators. In some variations, the identifier may identify a specific application for each applicator, such as indicating the particular body part for which the applicator is designed. In some variations, detecting the RFID identifier further includes instructing the controller to provide a selected pulsed current signal, wherein the selected pulsed current signal may include a pre-selected current signal, a pre-selected pulse duration, a pre-selected pulse frequency, or a combination thereof. The current-driven pulsed electromagnetic field (PEMF) apparatus having a single RF Driver/Controller and one or more applicators may include any components and may be configured in any combination as described herein.

In another aspect, a subject may be treated with a current-driven pulsed electromagnetic field (PEMF) apparatus having a single RF Driver/Controller and one or more applicators. Subject as referred to herein, may be a mammal, e.g. a human, dog, horse, cat, cow, and the like. The subject may be treated at any suitable location on his/her body, such as a foot, arm, knee, hand, torso, leg, and the like. The treatment may be one instance of treatment or may be a plurality of treatments distributed over a period of time to rehabilitate or accelerate healing. The treatments may be self-administered or may be administered by a caregiver. The current-driven pulsed electromagnetic field (PEMF) apparatus having a single RF Driver/Controller and one or more applicators used to treat the subject may be like any current-driven pulsed electromagnetic field (PEMF) apparatus described herein and may have any combination of components and any combination of configurations of components as described herein. The current-driven pulsed electromagnetic field (PEMF) apparatus may be operated using any of the methods described herein to operate such system.

Examples. FIG. 1A shows a schematic representation of a PEMF apparatus 100 having a single current-based RF Driver/Controller 110 which connects via a composite cable 115 to a multiplexer circuit (MUX) 120 configured to direct a pulsed current-based EMF signal to either of PEMF applicators 130 or 140. MUX 120 may be connected to more than two PEMF applicators. The RF Driver may include an RF oscillator, RF amplifier/modulator, impedance matching and a Low Pass Filter. MUX 120 may be connected to 2, 3, 4, 5, 6, 7, 8 or more PEMF applicators in the single current-based RF driven system. The MUX 120 may be physically located within one of the applicators 130, 140 of the apparatus 100. In some variations, it is advantageous to enclose MUX 120 within an enclosure of one of the applicators 130, 140 to minimize bulk and complexity of the system, thus simplifying use by a subject or a caregiver. The instrumentation and the cabling of a current-based PEMF apparatus is simplified, as there is no requirement to obtain RF feedback at the applicator itself. In the current-based system, the current delivered out to the applicator is the same as the current generated at the driver/controller 110, so a single current sensor may be disposed within the driver/controller 110 rather than requiring sensors within each applicator (for a voltage driven PEMF system). Rather than multiple twisted pairs of cables for multiple applicators as in a high-power PEMF system, only one composite cable including a coaxial cable for RF energetics and a twisted pair for carrying pulsed signal is needed to deliver the current-based pulse, as the return can come back in the same coaxial cable. The solid-state MUX circuitry distributes the RF energy to other applicators in a time multiplexing process. In some variations, the RF drive controller consists of a constant current source and a current sensor.

Figure 1B:
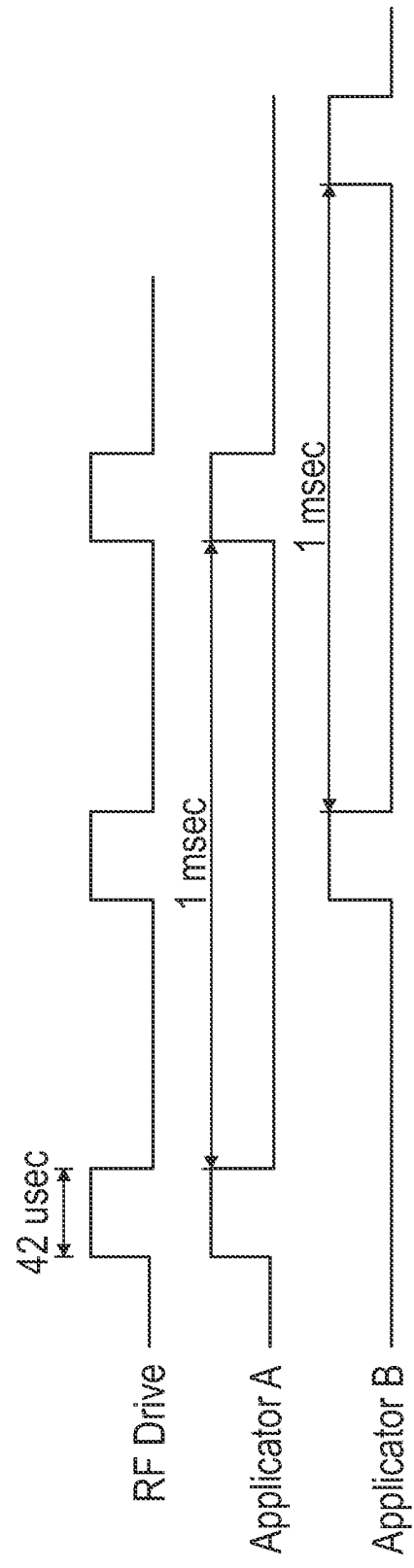
FIG. 1B is a schematic representation of the pulse characteristics for the apparatus of FIG. 1A permitting supply of PEMF signals to multiple applicators.

FIG. 1B shows an example of one, non-limiting pulse sequence that may be used in apparatus 100. The RF driver/controller 110 can provide a pulse of a selected current for a duration of 42 μsec every 0.5 msec. This may be switched at MUX120 between Applicator A (130) and Applicator B (140) so that each of Applicators A, B receives the 42 μsec pulse every 1 msec (4.2% duty cycle) offset from one another. The pulse width may be more than about 5 μsec; more than about 10 μsec, more than about 25 μsec, more than about 40 μsec, more than about 50 μsec, more than about 80 μsec, or about 100 μsec. The rate of pulsing may be varied to be less than once every 1 msec or more than once every 1 msec, depending on the biological effect selected.

FIG. 2 shows another variation of a single RF-driven current based PEMF apparatus 200, where the RF Drive circuitry connecting RF Driver 210 may be replaced with MUX 220. The composite cable will carry only digital signals to Applicators 230, 240 using DC power and there will be no RF. This makes the construction of the composite cable 215 simpler and less expensive. Also, using digital signals in composite cables 215 significantly reduces the problem seen when RF is transmitted along long cables, e.g. losing RF radiation. Apparatus 200 may be used to provide digital signal to Applicators 230, 240 either successively or simultaneously. Shown in FIG. 2 is each coil 233, 243 of the respective Applicators 230, 240, which receive the digital signal and emit the EMF signal including a magnetic field.

Shown in FIG. 2, but not so limited to apparatus 200, a remote control 250 (e.g., any kind of controller capable of wirelessly communicating with RF Driver/Controller 210) may be used to initiate, maintain and record usage of the PEMF apparatus 200, or any other PEMF apparatus described herein. Power supply 260 may be a connection to a wired electrical system or may be batteries.

Figure 3:
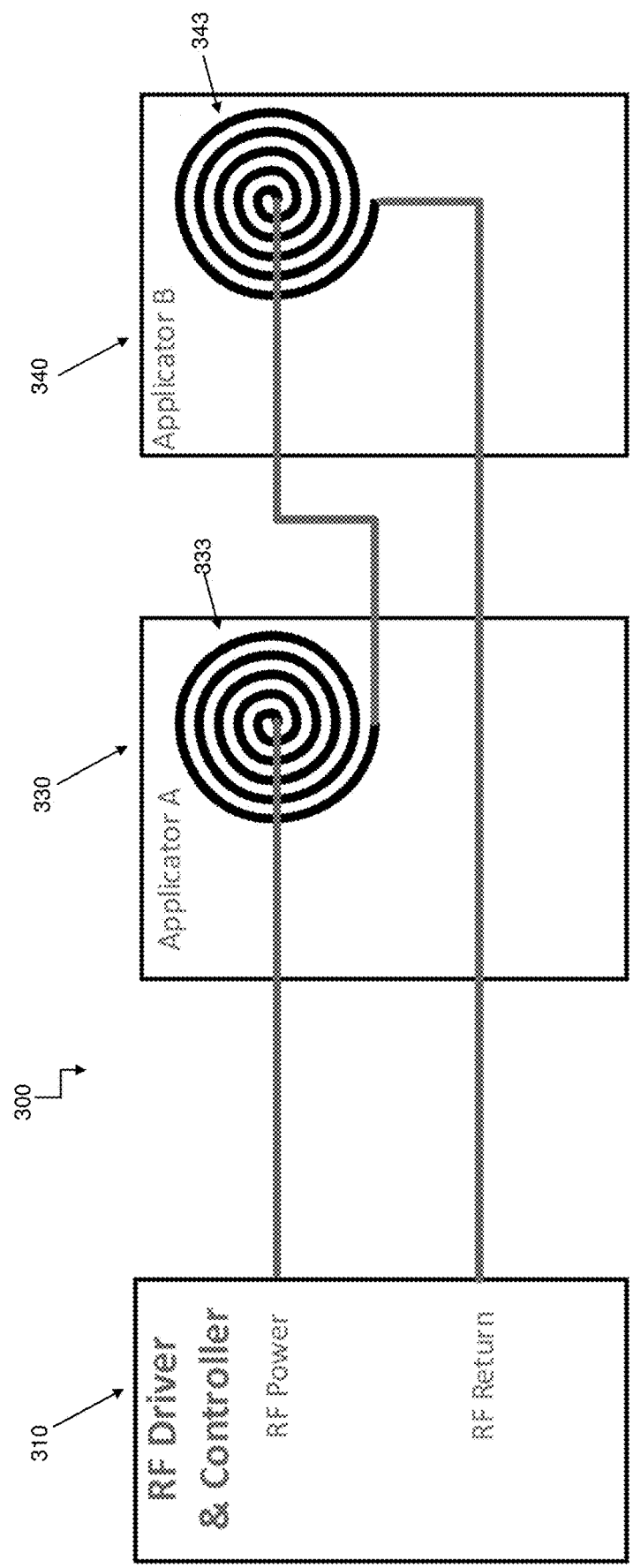
FIG. 3 is a schematic representation of a single current-based RF driver for a PEMF applicator apparatus according to some variations of the disclosure.

FIG. 3 is another variation of a single RF current-driven apparatus 300. The RF Driver/Controller 310 is connected to two or more Applicators 330, 340 where all of the coils 333, 343 are connected in series or in parallel to the RF Driver/Controller 310. RF power is applied to all coils simultaneously without the need for multiplexing.

Figure 4:
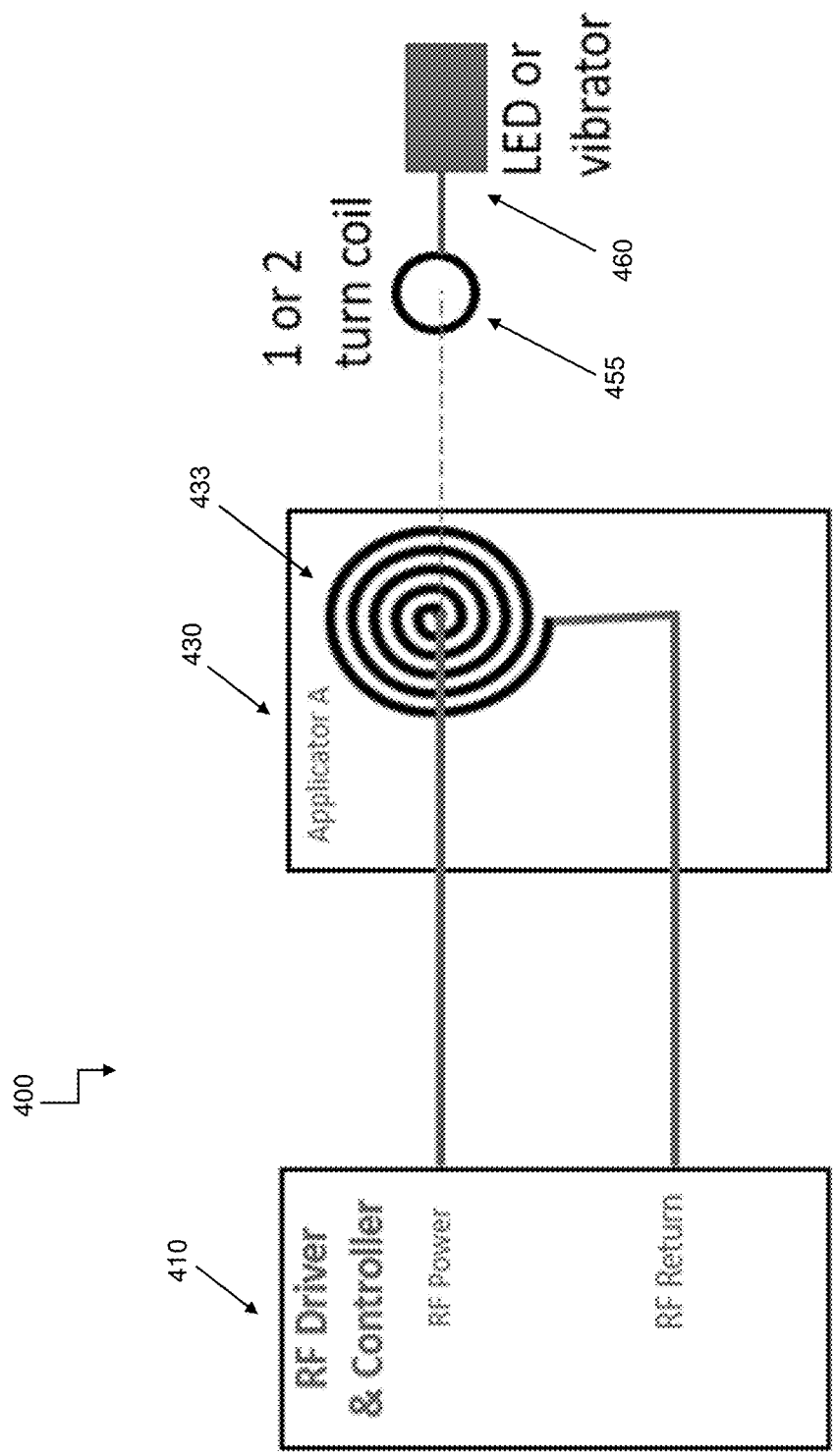
FIG. 4 is a schematic representation of a single current-based RF driver for a PEMF applicator apparatus according to some variations of the disclosure.

FIG. 4 shows another variation of a single RF current-driven apparatus 400, which is similar to apparatus 300. For simplicity, only one Applicator 430 is shown, but apparatus 400 may have one, two, three, four or more applicators, as described herein. Current signal is driven to Applicator 430, where the coil 433 emits an electromagnetic field signal. The applicator further includes a device, such as an LED or vibrator 460, indicating the presence of RF energy being applied to the body. The device is energized by magnetic induction similar to power transformer action, by coil 455, which may be a one or two turn coil.

FIG. 5 shows an electrostatically shielded radiator coil 500 which may be used with the coil 533, which may be like the coil of any applicator shown herein (233, 243, 333, 343, 433, or may be used with any coil of any applicator of a power driven PEMF system. A radiator coil produces both an electrical field as well as a magnetic field signal. The electrical field is affected by the capacitive effects of the particular body part upon which the applicator is applied, as well as by the path of approach for such application. These capacitive effects can change the coil impedance, causing loss of signal transmission and reflection of signal back towards the point of generation. This loss of efficiency can be prevented by use of an electrostatic shield around the radiator coil of the applicator. The radiator coil 533 of an applicator may be electrostatically shielded by having copper shields 503, 505 in the shape of a star on both sides of the coils. For example, alternating spokes of a first "star" shaped shield, labelled as 503 is disposed above the plane of radiator coil 533, while alternating spokes of a second "star" labelled as 505 is disposed underneath the plane of radiator coil 533. Advantageously, the electrostatic shield 503, 505 minimizes E-field (electrical field) without minimizing the magnetic field (H-field), e.g., the shielding has no effect on magnetic field signal. \

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A pulsed electromagnetic field (PEMF) apparatus for one or more applicators, the apparatus comprising:
   a controller configured to generate a pulsed current signal;
   one or more applicators coupled to the controller, each applicator comprising a coil configured to receive the pulsed current signal and to emit a PEMF signal comprising a magnetic field signal; and
   a current sensor configured to detect the pulsed current signal applied to the one or more applicators, wherein the controller is configured to maintain the pulsed current signal at a selected current based on feedback from the current sensor,
   wherein the controller further comprises an RFID reader and each of the one or more applicators comprises a unique RFID signature,
   and wherein the controller is further configured to identify a treatment for a specific body part associated with each unique RFID signature and select the pulsed current signal for generation based at least in part on the unique RFID signature.

2. The apparatus of claim 1, wherein the current sensor is within a housing shared with the controller.

3. The apparatus of claim 1, further comprising a composite cable configured to transmit digital signals from the controller to the one or more applicators, wherein the digital signals cause the one or more applicators to emit the PEMF signal.

4. The apparatus of claim 1, wherein the apparatus comprises at least two applicators, wherein the at least two applicators are connected in series with the controller.

5. The apparatus of claim 1, wherein the apparatus comprises at least two applicators, wherein the at least two applicators are connected in parallel with a single current-based radio frequency (RF) energy driver.

6. The apparatus of claim 1, wherein the one or more applicators comprises at least two applicators that are configured to emit the PEMF signal without interference from the other of the at least two applicators.

7. The apparatus of claim 1, wherein the controller further comprises a wireless remote controller.

8. The apparatus of claim 1, wherein the one or more applicators comprises an electrostatic shield about the coil configured to attenuate an emitted electric field.

9. The apparatus of claim 8, wherein the electrostatic shield attenuates at least about 30% of the emitted electric field.

10. The apparatus of claim 1, wherein at least one of the one or more applicators further comprises an indicator device energized by magnetic induction from the coil.

11. The apparatus of claim 10, wherein the indicator device comprises an LED or a vibrator device.

12. The apparatus of claim 1, wherein the unique RFID signature of each of the one or more applicators is configured to identify a specific application for each of the one or more applicators.

13. The apparatus of claim 1, wherein the unique RFID signature is configured to instruct the controller to provide a selected pulsed current signal, wherein the selected pulsed current signal comprises a pre-selected current signal, a pre-selected pulse duration, a pre-selected pulse frequency, or a combination thereof.

14. The apparatus of claim 1, wherein the apparatus is configured to provide an electromagnetic field having a magnetic field strength between 10 to 200 A/m.

15. The apparatus of claim 1, wherein the controller includes a current-based RF energy driver configured to provide an electromagnetic field having a magnetic field strength between 1 to 40 A/m or between 18 to 31 A/m.

16. The apparatus of claim 1, wherein the controller includes a single current-based RF energy driver configured to provide an electromagnetic field having a magnetic field strength between 60 to 80 A/m.

17. The apparatus of claim 1, wherein the pulsed current signal has a carrier frequency of about 27 MHz.

18. The apparatus of claim 1, wherein the pulsed current signal has a pulse width of between about 1 microsecond and about 200 microseconds.

19. The apparatus of claim 1, wherein the selected pulsed current signal includes a pre-selected pulse duration, a pre-selected pulse frequency, a pre-selected current signal, or a combination thereof.

20. A pulsed electromagnetic field (PEMF) apparatus for one or more applicators, the apparatus comprising:
- a controller configured to generate a pulsed current signal;
- one or more applicators coupled to the controller, each applicator comprising a coil configured to receive the pulsed current signal and to emit a PEMF signal comprising a magnetic field signal;
- an electrostatic shield about the coil of each of the one or more applicators, configured to attenuate an emitted electric field by at least about 30%; and
- a current sensor in the controller, wherein the current sensor is configured to detect the pulsed current signal applied to the one or more applicators, and wherein the controller is configured to maintain the pulsed current signal at a selected current based on feedback from the current sensor,
- wherein the controller further comprises an RFID reader and each of the one or more applicators comprises a unique RFID signature,
- and wherein the controller is further configured to identify a treatment for a specific body part associated with each unique RFID signature and select the pulsed current signal for generation based at least in part on the unique RFID signature.

* * * * *